United States Patent
Gertzman et al.

(10) Patent No.: US 6,911,212 B2
(45) Date of Patent: *Jun. 28, 2005

(54) MALLEABLE PUTTY AND FLOWABLE PASTE WITH ALLOGRAFT BONE HAVING RESIDUAL CALCIUM FOR FILLING BONE DEFECTS

(75) Inventors: Arthur A. Gertzman, Stony Point, NY (US); Moon H. Sunwoo, Old Tappan, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 489 days.

This patent is subject to a terminal disclaimer.

(21) Appl. No.: 09/983,526

(22) Filed: Oct. 24, 2001

(65) Prior Publication Data

US 2003/0206937 A1 Nov. 6, 2003

Related U.S. Application Data

(63) Continuation-in-part of application No. 09/515,656, filed on Feb. 29, 2000, which is a continuation-in-part of application No. 09/031,750, filed on Feb. 27, 1998, now Pat. No. 6,030,635, said application No. 09/515,656, and a continuation-in-part of application No. 09/365,880, filed on Aug. 3, 1999, now abandoned, which is a continuation of application No. 09/031,750, filed on Feb. 27, 1998, now Pat. No. 6,030,635.

(51) Int. Cl.⁷ .............. A61F 2/02; A61F 2/28
(52) U.S. Cl. .......... 424/426; 424/489; 523/115; 623/23.61; 623/23.62; 623/23.63
(58) Field of Search ................ 424/489, 423, 424/426; 523/116, 115; 623/23.61, 23.62, 23.63

(56) References Cited

U.S. PATENT DOCUMENTS

| | | | |
|---|---|---|---|
| 4,172,128 A | | 10/1979 | Thiele et al. |
| 4,191,747 A | | 3/1980 | Scheicher |
| 4,440,750 A | | 4/1984 | Glowacki et al. |
| 5,053,049 A | | 10/1991 | Campbell |
| 5,073,373 A | | 12/1991 | O'Leary et al. |
| 5,290,558 A | | 3/1994 | O'Leary et al. |
| 5,314,476 A | | 5/1994 | Prewett et al. |
| 5,356,629 A | | 10/1994 | Sander et al. |
| 5,507,813 A | | 4/1996 | Dowd et al. |
| 5,830,493 A | | 11/1998 | Yokota et al. |
| 6,030,635 A | * | 2/2000 | Gertzman et al. .......... 424/423 |
| 6,189,537 B1 | | 2/2001 | Wolfinbarger |
| 6,305,379 B1 | | 10/2001 | Wolfinbarger, Jr. |

* cited by examiner

*Primary Examiner*—Carlos A. Azpuru
(74) *Attorney, Agent, or Firm*—John S. Hale; Gipple & Hale

(57) ABSTRACT

The invention is directed toward a malleable bone putty and a flowable pastel composition for application to a bone defect site to promote new bone growth at the site which comprises a new bone growth inducing compound of partially demineralized lyophilized allograft bone material having a residual calcium content ranging from 4 to 8% dry weight. The bone powder has a particle size ranging from about 100 to about 800 microns and is mixed in a high molecular weight hydrogel carrier containing a sodium phosphate saline buffer, the hydrogel component of the carrier ranging from about 1.00 to 50% of the composition and having a molecular weight of about at least 700,000 Daltons. The composition has a pH between 6.8–7.4 contains about 25% to about 35% bone powder and can be additionally provided with BMP's.

70 Claims, No Drawings

MALLEABLE PUTTY AND FLOWABLE PASTE WITH ALLOGRAFT BONE HAVING RESIDUAL CALCIUM FOR FILLING BONE DEFECTS

RELATED APPLICATIONS

This is a continuation-in-part of U.S. patent application Ser. No. 09/515,656 filed Feb. 29, 2000 which is a continuation-in-part of U.S. patent application Ser. No. 09/031,750, filed Feb. 27, 1998 and issued into U.S. Pat. No. 6,030,635 on Feb. 29, 2000, the '656 Application also being a continuation-in-part of U.S. patent application Ser. No. 09/365,880, filed Aug. 3, 1999, now abandoned, which is a continuation application of U.S. patent application Ser. No. 09/031,750 which has issued into U.S. Pat. No. 6,030,635.

FIELD OF INVENTION

The present invention is generally directed toward a surgical bone product and more specifically is a flowable paste and a malleable putty using partially demineralized allograft bone particles having a residual calcium content of about 3 to about 8 percent mixed in a fluid carrier having an isotonic phosphate buffer and a viscous excipient derived from the class of biomaterials known as hydrogels.

BACKGROUND OF THE INVENTION

Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Malleable putty is used to correct surgical defects that may be caused by trauma, pathological disease, surgical intervention or other situations where defects need to be managed in osseous surgery. It is important to have the defect filler in the form of a stable, viscous putty to facilitate the placement of the bone growth medium into the surgical site which is usually uneven in shape and depth. The surgeon will take the putty on a spatula or other instrument and trowel it into the site or take it in his/her fingers to shape the bone inducing material into the proper configuration to fit the site being corrected. It is also important that the defect filler be biocompatible, have the correct osmolality and pH and not cause any additional trauma at the surgical site.

Many products have been developed in an attempt to treat this surgical need for a biocompatible bone putty or gel. One such example is autologous bone particles or segments recovered from the patient. When removed from the patient, the segments or bone particles are wet and viscous from the associated blood. This works very well to heal the defect but requires significant secondary surgery resulting in lengthening the surgery, extending the time the patient is under anesthesia and increasing the cost. In addition, a significant increase in patient morbidity is attendant in this technique as the surgeon must take bone from a non-involved site in the patient to recover sufficient healthy bone, marrow and blood to perform the defect filling surgery. This leads to significant post-operative pain.

Another product group involves the use of inorganic materials to provide a matrix for new bone to grow at the surgical site. These inorganic materials include hydroxyapatite obtained from sea coral or derived synthetically. Either form may be mixed with the patient's blood and/or bone marrow to form a gel or a putty. Calcium sulfate or plaster of Paris may be mixed with water to similarly form a putty. These inorganic materials are osteoconductive but are bioinert. The calcium sulfate materials absorb slowly but the other materials do not absorb or become remodeled into natural bone. They consequently remain in place indefinitely as a brittle, foreign body in the patient's tissue.

Allograft bone is a logical substitute for autologous bone. It is readily available and precludes the surgical complications and patient morbidity associated with autologous bone as noted above. Allograft bone is essentially a collagen fiber reinforced hydroxyapatite matrix containing active bone morphogenic proteins (BMP) and can be provided in a sterile form. The demineralized and partially demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

It is well known in the art that for several decades surgeons have used a patient's own blood as a vehicle in which to mix the patient's bone chips or bone powder, or demineralized bone powder so as to form a defect filling paste. Blood is a useful carrier because it is available from the bleeding operative site, is non-immunogenic to the patient and contains bone morphogenic proteins which facilitate wound healing through new bone growth. However, stored blood from other patients has the deficiencies that any blood transfusion would have; such as blood type compatibility, possibility of transmission of disease and an unknown concentration of BMP which is to a great extent dependent upon the age of the donor.

While blood contains from forty percent (40%) to fifty percent (50%) cell mass, it is a satisfactory carrier for demineralized bone powder because it contains both mono- and polysaccharides which contribute to the blood viscosity and provide the bulk viscosity to the paste created by mixing the bone powder and blood. Specific monosaccharides in blood are glucose at a concentration of 60–100 mg/100 ml (0.1%) and polysaccharides such as hexose and glucosamine at approximately 0.1%. Glucuronic acid is also present at approximately 0.4–1.4 mg/100 ml (average 0.01%).

The problems inherent with using the patients blood as a carrier for demineralized bone powder are the difficulties of mixing the same at the operating site, the difficulty in obtaining a bone paste consistency which can be easily applied to the surgical area, the guesswork in mixing a usable composition at the site and the problem of having a bone putty or gel which will promote optimum bone replacement growth and not be carried away by the body fluids at the operation site or simply fall out of the bone defect site. In an attempt to solve these and other problems, there have been a number of other attempts using other alternative mixtures and compositions.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a gel, GRAFTON®, a registered trademark of Osteotech Inc., which is a simple mixture of glycerol and lyophilized, demineralized bone powder having little to no residual calcium, averaging less than 0.01% and having a particle size in the range of 0.1 cm to 1.2 cm (1000 microns to 12,000 microns) as is disclosed in U.S. Pat. No. 5,073,373.

GRAFTON works well to allow the surgeon to place the allograft bone material at the site. However, the carrier, glycerol has a very low molecular weight (92 Daltons) and is very soluble in water, the primary component of the blood which flows at the surgical site. Glycerol also experiences a marked reduction in viscosity when its temperature rises from room temperature (typically 22° C. in an operating room) to the temperature of the patient's tissue, typically 37° C. This combination of high water solubility and reduced viscosity causes the allograft bone material with a glycerol carrier to be "runny" and to flow away from the site almost immediately after placement; this prevents the proper retention of the bone material within the site as carefully placed by the surgeon. Furthermore concerns about the neurotoxic behavior of glycerol have been noted in Spine Vol. 26, No. 13 Jul. 1, 2001 in an editorial by the Deputy Editor, C. A. Dickman, M.D. which has a clinical recommendation to limit the dose of GRAFTON®, avoid use in certain medical situations, avoid use with small children and to avoid direct contact of GRAFTON® with exposed spinal nerves.

These problems with GRAFTON gel have been attempted to be resolved by using a much larger particle size of allograft bone, specifically lamellae or slivers of bone created by milling or slicing the bone before mixing it with the glycerol carrier. This improves both the bulk viscosity and the handling characteristics of the mixture but still leaves the problem of the fast rate of dissipation of the carrier and some bone due to the solubility of the glycerol carrier.

U.S. Pat. No. 5,290,558 discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

Hence, the advantages of using the smaller bone particle sizes as disclosed in the U.S. Pat. No. 5,073,373 gel patent were compromised by using bone lamellae in the shape of threads or filaments and retaining the low molecular weight glycerol carrier. This later prior art is disclosed in U.S. Pat. Nos. 5,314,476 and 5,507,813 and the tissue forms described in these patents are known commercially as the GRAFTON® Putty and Flex, respectively.

The use of the very low molecular weight glycerol carrier also requires a very high concentration of glycerol to be used to achieve the bulk viscosity. Glycerol and other similar low molecular weight organic solvents are toxic and irritating to the surrounding tissues.

U.S. Pat. No. 6,189,537 is directed toward a process of demineralization of ground bone particles or pieces of cancellous or cortical bone which permits the controlled and reproducible demineralization of bone to produce bone having a residual calcium level of approximately 2% (1.8% to 2.5%) by dry weight of bone which was found to be osteoinductive as assayed using in vivo and in vitro assays of osteoinductivity. The controlled-flow apparatus includes one or more solution containers which supply solutions to be pumped into one or more vessels filled with tissue samples to be extracted. Solvent outflowing from the vessels can be monitored for pH, calcium ion concentration or conductivity as a basis for determining when extraction is complete allowing production of a partially demineralized bone material with a designated range of residual calcium.

U.S. Pat. No. 5,356,629 discloses making a rigid gel in the nature of a bone cement to fill defects in bone by mixing biocompatible particles preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteoinductive agent such as demineralized bone powder, in addition to morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used. However, the biocompatible particles used in this reference are used in a much greater weight ranging from 35% to 70% by weight then that taught by the present invention. The reference is directed toward a cement used for implantation of hip prosthesis and is not used to promote bone growth.

U.S. Pat. No. 5,830,493 is directed toward a composite porous body (hyaluronic acid listed in a group of compounds) comprising a porous frame and a surface layer comprising a bioabsorbable polymer material formed on the surface. A bone morphogenetic protein (BMP) is carried on the surface and inside of the composite porous body. There is no use of demineralization of bone.

U. S. Pat. No. 5,053,049 discloses a composition for treating bone defects comprising demineralized bone osteogenic powder that has been tanned and used with any suitable biologically compatible or inert carrier which may include polysaccharides. The tanning can be by glutaraldehyde or different agents including formaldehyde or alcohol.

Another attempt to solve the bone composition problem is shown in U.S. Pat. No. 4,172,128 which discloses demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35 C. and will solidify when brought down to body temperature. Example 25 of the patent notes that mucopolysaccharides produce pronounced ionotropic effects and that hyaluronic acid is particularly responsible for spatial cross-linking. Unfortunately this bone gel is difficult to manufacture and requires a premolded gel form.

U.S. Pat. No. 4,191,747 teaches a bone defect treatment with coarsely ground, denatured bone meal freed from fat and ground into powder. The bone is not demineralized and retains its complete mineral content. The bone meal is mixed with a polysaccharide in a solution of saline and applied to the bone defect site.

U.S. Pat. No. 4,440,750 discloses the use of demineralized osteogenic bone powder in a physiological carrier such as saline to treat a bone defect site to promote new bone growth.

Another prior art product is the formulation of demineralized allograft bone particles in collagen. Both bovine and human collagen have been used for this application. Bovine collagen carries the risk of an immunogenic reaction by the recipient patient. Recently, it has been found that a disease of cattle, bovine spongioform encephalopathy (mad cow disease) is transmitted from bovine tissue to humans. Thus, bovine tissue carries a risk of disease transmission and is not a desirable carrier for allograft tissue.

Human collagen is free of these animal based diseases. However, collagen absorbs slowly in the human body, particularly in a bony site with usually a low degree of vascularity. The slow absorption of collagen can delay the growth of new bone and result in the formation of scar tissue at the site. This could result in a non-bony healing and a result with much less tensile strength.

Accordingly, the prior art as embodied in the glycerol and other carrier based technology to deliver demineralized and mineralized allograft bone to a surgical osseous site is replete with problems and only partially addresses the problems inherent in the correcting surgical defects which are solved in the present invention.

SUMMARY OF THE INVENTION

The subject formulation is a complex mixture of a partially demineralized bone matrix (DBM) having a residual calcium preferably ranging from about 4% to about 8% and a viscous hydrogel based on a high molecular weight material mixed with a sodium based phosphate buffer acting as a carrier or delivery vehicle for the agent, DBM. The viscous formulation is designed to present the DBM, and its bone morphogenetic proteins (BMP), and the macrostructure of the highly porous DBM itself to serve both as an osteoconductive matrix and to signal the patient's tissue and cells to initiate the growth of new bone (osteoinduction). The formulation is used primarily in contact with bleeding bone. This condition is created either from trauma or a surgical procedure, that may involve drilling, sawing, grinding or scraping the bone to achieve a bleeding condition. In surgery, the bone is traumatized or surgically cut exposing blood capillaries, Haversian canals (micro-channels in the bone), periosteum (the protective tissue lining around bone), muscle and other structures in the surgical site. Bleeding at the site is considered a favorable condition to enhance healing of the wound site by bringing to the site the patient's own cytokines, i.e., proteins and other molecules which are the body's mechanism to carry out the healing process. Any interference with the blood cell mechanism would be considered non-biocompatible and an adverse outcome.

In order for the DBM to be osteoinductive, interference either from the traumatized cells or the formulation must be at a minimum, i.e., a biocompatible condition should be established and maintained. Several specific properties have been established in the composition formulation to create a functional material. These properties pertain to both physical characteristics and to the achieving of a biocompatible or physiologically friendly condition.

The selection of high molecular weight hydrogels allows the use of the preferred small particle size granules of partially demineralized allograft bone. These small particles pack better in the wound defect and absorb quickly thereby allowing the bone defect to be remodeled into the natural bone of the patient and the specific residual calcium allows faster bone repair.

It is an object of the invention to utilize a partially demineralized bone component in a size that is useful to achieve the desired malleability characteristics that maximizes the amount of bone in the formulation without creating a gritty, less malleable characteristic which is difficult to handle by the surgeon.

It is another object of the invention to utilize a partially demineralized bone component with a residual calcium content in the range of 4 to 8%.

It is an additional object of the invention to use a non toxic aqueous solution carrier with a sodium phosphate buffer for the bone particles to present the composition in a state of physiological osmolality at the wound site.

It is also an object of the invention to create a bone defect material which can be easily handled by the physician and does not degenerate when contacting blood flow at the surgical site.

It is another object of the invention to create a bone defect material which does not interfere with healing at the wound site and promotes faster bone formation.

It is still another object of the invention to create a bone defect material which has a stable viscosity from 22° to 37° C.

It is an additional object of the invention to create a bone defect material with an isotonic pH.

It is another object of the invention to use cortical/cancellous chips in the form of irregularly shaped polyhedra with an edge dimension of up to 5 mm.

It is yet another object of the invention to use a sodium salt with the demineralized bone composition to aid in healing at the bone defect site.

It is still another object of the invention to provide a premixed bone putty/paste which can be shaped and used at the point of surgery.

DESCRIPTION OF THE INVENTION

The present invention and best mode is directed towards a partially demineralized bone material (DBM) composition having a residual calcium content ranging between about 3 to about 10%, preferably 4 to 6% mixed with a high molecular weight hydrogel and a phosphate buffer to heal bone defects. The term demineralization as used in relatoin to treatment of bone up through at least the middle of the 1990's was construed by those skilled in the art to mean that all or substantially all of the mineral content of bone was removed leaving the bone with a residual calcium approaching 0.0% but less than 0.01%. In the late 1990's the term demineralized was used to describe bone which had been subjected to demineralization and had a greater residual calcium content. The terms "partially demineralized" or "demineralized" as used in this description of the invention are used to refer to bone after mineral removal, which has residual calcium left therein in an amount of at least 3% but less than 10%.

A bone putty and paste with a useful bulk viscosity has been achieved by using a high molecular weight class of soluble biomaterial, hydrogel. The use of high molecular weight hydrogels allows the achievement of a useable bone putty or paste with a 1.0–5.0% concentration of the hydrogel in the carrier, depending upon the hydrogel used. Lower weight hydrogels can have a higher percentage concentration in the carrier. The balance of the carrier formulation is an aqueous solution and preferably includes the addition of a material component, namely, a sodium based phosphate buffer in a sterile saline or salt carrying water which avoids the toxic problems with the high concentrations of the low molecular weight organic solvents of the prior art.

In the preferred embodiment, the DBM is prepared by soaking the bone segments for several minutes in a container with enough sterile ethanol to cover the tissue. The bone segments are milled and placed in a sieve to size the milled bone to 100–800 microns or coarse ground to achieve cortical/cancellous chips in the form of irregularly shaped polyhedra with an edge dimension up to 5 mm. The milled bone material is placed in mixing container and cleaned with a 5:1 ratio of 3% Hydrogen Peroxide and stirred for 15 minutes, removed and rinsed with a minimum of 3000 ml of sterile water. The rinsed bone powder is placed back into the cleaned mixing container and at least 1000 ml of 70% sterile ethanol is added and the solution is mixed for 30 minutes. The bone powder is then transferred into a No. 70 sieve and an open vacuum is applied to the bottom of the sieve and the bone powder is dried for 20 minutes. The dried bone powder is transferred to the demineralization process where it is weighed. The bone weight in grams is compared to a chart which determines the acid volume to be applied which is approximately 1 gram equals approximately 16 ml of acid. The bone powder is mixed with 0.6N HCl for about 2½ hours to achieve maximum bone powder surface engagement with the HCl to remove most of the mineral content.

When Cortical/cancellous bone chips are used the bone chips are transferred to the demineralization process where the same is weighed. Bone chips are mixed with 0.6N HCl at a 1:16 ratio and treated for a longer time of up to 8 hours. Alternatively cortical/cancellous bone chips are mixed with 0.6N HCl which is calculated at a 1:30 ratio and treated for 3 to 5 hours to control the residual calcium content in the range of 3% to 8%.

The bone material is then rinsed with water and 800 ml of sodium phosphate dibasic buffer solution is added to the mixture and the mixture is stirred for about 1 hour to stabilized the pH at around 7.0. The buffered bone powder is then rinsed with sterile water several times leaving a preferred residual calcium content ranging from about 3.0% to about 8% by dry weight of the bone with an optimum preferred residual calcium content of 4% to 6%.

The combination of the respective sized components of partially demineralized, lyophilized, allograft bone when mixed with very low concentrations of high molecular weight stable viscosity hydrogels in a suitable carrier produces a malleable putty with and/or a flowable paste clinically useful bone inducing properties. The malleable property permits the surgeon to shape the quantity of bone putty or paste to exactly fit the surgical defect. Manipulation of the "lump" of bone putty may be done without it sticking to the gloves of the surgeon, behaving somewhat like a wet clay used in sculpting.

It is an important aspect of the present invention that the implant matrix must remain at the wound site and not be washed away by the flowing blood and other fluids brought to the site by the healing mechanism. This is achieved by both the viscous and hydrogel state of the carrier. While viscous, the aqueous carrier is a high molecular weight macromolecule held together with water linkages (hydrogen bonds) and is not readily dissolved and washed away by the blood and fluids at the wound site.

Thus, the DBM will not be dissipated by being washed away and will be present to be osteoinductive.

The amount of DBM is maximized to achieve the optimum balance of osteoinductivity and physical handling properties. Too much matrix bone creates a gritty or sandy condition in which the DBM is not ideally enclosed by the surrounding viscous matrix and the DBM bone particles would be too easily washed away. Conversely, if the bone concentration is too low, the osteoinductivity would be less than optimum. Bone concentration in the composition can be in the range of about 20% to about 50% and preferably ranges from about 25% to about 35%.

These and other alternate embodiments of the invention overcome the two basic deficiencies of the glycerol carrier and bone particle flowable compositions used in the prior art: first, the low molecular weight of glycerol; and second, the use of large particles or lamellae to achieve the preferred bulk viscosity. The types of demineralized bone used in the invention are cortical and corticocancellous bone powder and chips.

The primary role of the carrier is to serve as a delivery vehicle. The bulk viscosity of the carrier achieves the design goal of good handling properties by balancing the molecular weight and concentration of the hydrogel used in the formulation. For example, a very high molecular weight hydrogel would use a lower concentration compared to a formulation in which the hydrogel molecular weight was considerably lower with a higher concentration used to achieve the same bulk viscosity. The present invention can use HA having a molecular weight of about $7.0 \times 10^5 - 3.0 \times 10^6$ Daltons. The nominal formulation uses a 700,000 Dalton molecular weight hydrogel (sodium hyaluronate or HA). The terms HA or sodium hyaluronate should be construed throughout this application as encompassing sodium hyaluronate, hyaluronic acid, pharmaceutically acceptable salts of hyaluronic acid, derivatives of hyaluronic acid and pharmaceutically acceptable salts of hyaluronic acid derivatives and mixtures thereof. This HA material is used at a 1–5% concentration in water or phosphate buffered saline to achieve the bulk viscosity required for the paste or putty formulation.

If the balance of molecular weight and concentration were not optimized, the results would be a runny, excessively fluid formulation that would not stay at the surgical site. When hydrogel molecular weights are low, a high concentration is necessary to give a good bulk viscosity. Unfortunately concentrations with such a corresponding viscosity above this level are extremely difficult to filter to achieve sterility required by a surgical implant. Guidelines for sterility require a statistical assurance of no more surviving microorganisms than one in one million. This cannot be achieved above a concentration of about 5–6% hydrogel of a molecular weight of 700,000 Dalton. Very much higher concentrations would result in a semi solid not having desirable handling properties as it would lose the desirable malleability required for a defect filling formulation.

Hydrogels of a higher molecular weight can also be effectively used at concentrations as low as 0.25 to 1.5% to achieve a successful bulk viscosity of 120,000 cps to 270,000 cps for putty and 2,000 cps to 15,000 cps for paste. At these concentrations, molecular weights of the hydrogel as high as 3–5 million Dalton can be used. In addition to the high molecular weight hydrogels, lesser molecular weight hydrogels can also be used.

Such lesser weight hydrogels are 1) Chitosan about 10,000 to 300,000 Daltons; 2) Sodium Alginate about 10,000 to 300,000 Daltons; 3) Dextran about 40,000 Daltons; 4) carboxymethylcellulose (CMC) about 20,000 to 40,000 Daltons and 5) hydroxypropylmethylcellulose (HPMC) about 20,000 to 40,000 Daltons. Other non hydrogel substances which can be used are Gelatin and Collagen.

The natural condition for blood plasma as well as synovial fluid, cerebrospinal fluid, aqueous humor (fluid within the globe of the eye) is at a pH of 7.3–7.4 (reference, *Principles of Biochemistry*, Chapters 34 & 35; White, Handler and Smith, McGraw Hill, NY, 1964). At very slight changes in pH, blood cells will shift their equilibrium of hemoglobin. This hemoglobin concentration will change over the small pH range of 7.3 to 7.7 (White et al p. 664). In addition, at significantly lower pH values in the acidic range, protein molecules will denature, i.e., degrade. Thus, it is important to maintain any surgical implant which is intimate contact with blood at a biocompatible condition of about pH 7.2–7.4.

It is important to note that the body has many complex and redundant mechanisms to maintain its biochemical balance. The blood pH can be adjusted by several means to its normal, physiologic pH. Hence the presence of a non-physiologic material at the site of a bleeding bone wound will eventually be overcome and any non-biocompatible condition will return to normal pH. It is a teaching of this invention that the preferred formulation will start out and maintain physiologic pH without stressing the body's biochemical mechanisms when the bone composition material is applied at the wound site.

In achieving physiologic pH, the formulation uses a phosphate buffer based on an aqueous system of the two phosphate anions, $HPO_4^{-2}$ and $H_2PO_4^{-1}$. This buffer system is used both to neutralize the acid used to demineralize the bone and to buffer the sodium hyaluronate viscous hydrogel carrier. It is important to neutralize the acid (hydrochloric acid) used to demineralize the bone so as to assure that there is no residue of this very strong acid which could overwhelm the buffering capacity of the phosphate system used to buffer the sodium hyaluronate carrier.

The pH is adjusted to the physiologic 7.2–7.4 pH by using either or both of dibasic sodium phosphate or monobasic sodium phosphate and adjusting the solution with saline, i.e., a sodium chloride solution. The sodium chloride is chosen instead of only water so as to control the final osmolality of the formulation to preclude dehydration of the surrounding cells.

The present invention uses sodium salts of the phosphate buffer. This is to create an equilibrium system at the wound site which will draw in calcium ions necessary to grow new bone. The mechanism to achieve this is based on the LeChatelier corollary to the *Principle of Chemical Equilibrium*: *When a factor (temperature, pressure, concentration, etc.) determining the equilibrium of a system is altered, the system tends to change in such a way as to oppose and partially annul the alteration in this factor*. (reference, *General Chemistry*, McCutcheon, Seltz and Warner, Van Nostrand, NY, 1944; p. 248).

The buffer solution will assist in stimulating the formation of bone growth at a bone defect site at a faster rate than a composition without such a buffer. Studies have shown that the presence of phosphate ions accelerates the formation of hydroxyapatite, the principle component of bone. Fulmer, M. T. et al "Effects of Na2HPO4 and Na H2PO4 on hydroxyapatite formation," *J. Biomed. Maters, Res., Vol.* 27 1095–1102 (1993).

This principal manifests at the bone wound site as follows: The buffer introduced contains sodium and phosphate ions which will remain in solution due to the high solubility of sodium phosphate. Calcium ions in the extracellular fluid will react with the phosphate ions to result in the precipitation of insoluble calcium phosphate salt. More phosphate ions will ionize from the associated state of the phosphate buffer to introduce more phosphate ions that will, in turn react with more calcium and precipitate yet more insoluble calcium phosphate. The calcium phosphate will deposit at the wound site where the buffered formulation was placed by the surgeon. This results in an increase in the presence of calcium at the wound site. The bone regeneration mechanism will utilize calcium starting 7–10 days after the wound starts healing by the well-known osteochondral healing mechanism. Hence, the selection of the sodium phosphate buffer to achieve the physiologic pH provides a means to increase the calcium concentration in the precise location where calcium will be needed to grow new bone.

Thus, the invention induces the presence of soluble calcium at the bone defect site. This will encourage new bone growth through the normal biochemical mechanism. Soluble calcium can be attracted to the surgical site by using a sodium phosphate buffer of pH 6.8–7.2 in lieu of isotonic saline. The phosphate buffer attracts calcium cations to the site from the surrounding healthy bone and creates an equilibrium concentration of the calcium precisely at the site of healing where it is most desirable to grow new bone.

It is a well known principal of physiology that osmotic pressure must be maintained within a narrow range to assure healthy conditions for the many cell types present in normal or surgically wounded cells. The condition of normal osmotic pressure is referred to as an isotonic state and is quantified in humans by the value of about 300 mOsmol/Kg. The sodium hyaluronate (HA) formulation is buffered to isotonic conditions using sodium chloride as the ionic salt to supplement the sodium phosphate. Were the sodium hyaluronate formulation to be buffered without the supplemental saline, the final hydrogel would only reach an osmolality of less than 50 mOsmol/Kg.

At this low osmolality, the extra cellular environment at the wound site would be in a state of hypotonicity and result in the inflow of large quantities of water to the cells and blood cells at the wound site to normalize the osmotic pressure. This will result in a greater than optimum degree of hydration of the cells and inhibit wound healing in general and bone growth in particular. Hemolysis may occur due to excess fluid in the cells.

Other, commercial bone defect fillers are either non-isotonic or worse, are completely anhydrous. The anhydrous state will result in a massive hydration of the site. This will result in an edematous condition. This condition would result in both diluting the DBM (washes it away) and massive dilution of the extracellular fluids. On a macro level, edema is seen as swelling at the site and may be painful to the patient.

The subject formulation has been tested for resistance to hemolysis in a test based on direct blood contact; the results were negative, i.e., the formulation was found to be non-hemolytic. The commercial, anhydrous formulation based on anhydrous glycerol is hemolytic by the same test protocol. The observation of hemolytic behavior by the glycerol based commercial bone filler may be due to the acidic pH (about 4.5) alone, or to a combination of the acidic pH and the non-isotonic state of the material as it enters the wound site.

Sodium hyaluronate in the form of the sodium salt is generally described as a glycosaminoglycan (GAG). It is envisioned that suitable amounts of bone morphogenic proteins (BMP) can be added to either the paste or putty at any stage in the mixing process to induce accelerated healing at the bone site. BMP directs the differentiation of pluripotential mesenchymal cells into osteoprogenitor cells which form osteoblasts. The ability of freeze dried demineralized cortical bone to transfer this bone induction principle using BMP present in the bone is well known in the art. However, the amount of BMP varies in the bone depending on the age of the bone donor and the bone processing. Sterilization is an additional problem in processing human bone for medical use as boiling, autoclaving and irradiation over 2.0 mrads is sufficient to destroy or alter the BMP present in the bone matrix.

In conducting experiments, it was found that a paste product with optimal formability and handling properties could have a sodium hyaluronate molecular weight ranging from about 700,0000 to about 1,200,000 Daltons with a sodium hyaluronate concentration ranging from about 1.0— about 2.0% with a partially demineralized allograft bone concentration having a residual calcium of from 3 to 8% ranging from 25–27% w/w with a particle size of 100–800 microns. This resulted in HA solution viscosities ranging from about 1,800 cps to about 13,000 cps. It was also found that a putty product with optimal formability and handling properties would have a molecular weight ranging from about 700,000 to about 1,200,000 Daltons with a sodium hyaluronate concentration ranging from 2.0–5.0% with a partially demineralized allograft bone concentration having a residual calcium of from 3 to 8% ranging from 30–33% w/w with various particle size. This resulted in HA solution viscosities ranging from about 6,000 cps to about 275,000 cps.

Any number of medically useful substances can be used in the invention by adding the substances to the composition at any steps in the mixing process or directly to the final composition. Such substances include collagen and insoluble collagen derivatives, hydroxy apatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin. It is also envisioned that amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments, living cells such as chondrocytes, blood cells, bone marrow cells, mesenchymal stem cells, natural extracts, tissue transplants, bioadhesives, transforming growth factor (TGF-beta), platelet derived growth factor (PDGF), osteopontin, fibroblast growth factor (FGF), insulin-like growth factor (IGF-1); growth hormones such as somatotropin; bone digestors; antitumor agents; fibronectin; cellular attractants and attachment agents; immuno-suppressants; permeation enhancers, e.g. fatty acid esters such as laureate, myristate and stearate monoesters of polyethylene glycol, enamine derivatives, alpha-keto aldehydes can be added to the composition.

EXAMPLES OF THE INVENTION

In the following examples the molecular weight of the various carrier components used is as follows:

| | |
|---|---|
| 1) Sodium Hyaluronate | $7.0 \times 10^5 - 2.6 \times 10^6$ Daltons |
| 2) Chitosan | $1.0 \times 10^4 - 3.0 \times 10^5$ Daltons |
| 3) Sodium Alginate | $1.0 \times 10^4 - 3.0 \times 10^5$ Daltons |
| 4) Dextran | $4.0 \times 10^4$ Daltons |
| 5) Carboxymethylcellulose | $2.0 \times 10^4 - 4.0 \times 10^4$ Daltons |
| 6) Hydroxypropylmethylcellulose | $2.0 \times 10^4 - 4.0 \times 10^4$ Daltons |
| 7) Gelatin | |
| 8) Collagen | |

A. Malleable Putty and Flowable Paste of Partially Demineralized Cortical Allograft Bone

Example I

A malleable putty of hyaluronic acid 4% with 100–800 micron sized demineralized cortical allograft bone powder having a residual calcium weight of 0.95% constituting approximately @ 32% total weight percentage of the composition.

The example was formulated with 66 grams of freeze dried demineralized cortical allograft bone of particle size of 100–800 microns mixed into 140.3 grams of a 4% solution of hyaluronic acid (mol. wt, approximately 700,000 Daltons) in phosphate buffered saline. The bone component is added to achieve a bone concentration of approximately 32%(w/w). The solution is well mixed and allowed to stand for 2–3 hours at room temperature. This provides a malleable putty with a penetration unit of 61 and excellent formability properties and a pH of 7.2.

Example II

A malleable putty of hyaluronic acid 4% with 100–800 micron sized demineralized cortical allograft bone powder having a residual calcium weight of 4.01% constituting approximately @ 32% total weight percentage of the composition.

The example was formulated with 69 grams of freeze dried demineralized cortical allograft bone of particle size of 100–800 microns mixed into 146.6 grams of a 4% solution of hyaluronic acid (mol. wt, approximately 700,000 Daltons) in phosphate buffered saline. The bone component is added to achieve a bone concentration of approximately 32%(w/w). The solution is well mixed and allowed to stand for 2–3 hours at room temperature. This provides a malleable putty with a penetration unit of 66 and excellent formability properties and a pH of 7.0.

Example III

A malleable putty of hyaluronic acid 4% with 100–800 micron sized demineralized cortical allograft bone powder having a residual calcium weight of 7.64% constituting approximately @ 32% total weight percentage of the composition.

The example was formulated with 122 grams of freeze dried demineralized cortical allograft bone of particle size of 100–800 microns mixed into 259.3 grams of a 4% solution of hyaluronic acid (mol. wt, approximately 700,000 Daltons) in phosphate buffered saline. The bone component is added to achieve a bone concentration of approximately 32%(w/w). The solution is well mixed and allowed to stand for 2–3 hours at room temperature. This provides a malleable putty with excellent formability properties and a pH of 7.0.

Example IV

A malleable paste of hyaluronic acid 4% with 100–800 micron sized demineralized cortical allograft bone powder having a residual calcium weight of 4.00% constituting approximately @ 27% total weight percentage of the composition.

The example was formulated with 70 grams of freeze dried demineralized cortical allograft bone of particle size of 100–800 microns mixed into 189.3 grams of a 4% solution of hyaluronic acid (mol. wt, approximately 700,000 Daltons) in phosphate buffered saline. The bone component is added to achieve a bone concentration of approximately 27%(w/w). The solution is well mixed and allowed to stand for 2–3 hours at room temperature. This provides a malleable putty with excellent formability properties and a pH of 7.2.

Example V

A malleable paste of hyaluronic acid 4% with 100–800 micron sized demineralized cortical allograft bone powder having a residual calcium weight of 7.78% constituting approximately @ 27% total weight percentage of the composition.

The example was formulated with 16 grams of freeze dried demineralized cortical allograft bone of particle size of 100–800 microns mixed into 43.3 grams of a 4% solution of hyaluronic acid (mol. wt, approximately 700,000 Daltons) in phosphate buffered saline. The bone component is added to achieve a bone concentration of approximately 27%(w/w). The solution is well mixed and allowed to stand for 2–3 hours at room temperature. This provides a malleable putty with excellent formability properties and a pH of 7.2.

Example VI

A malleable putty of sodium alginate 5% with 100–800 micron demineralized cortical allograft bone powder having a residual calcium weight of 3 to 8% @ 30% total weight percentage of the composition.

The example was formulated with 1 gram of freeze dried demineralized cortical allograft bone of particle size of 100–800 microns is mixed into 2.33 grams of a 5% solution of sodium alginate (mol. wt, approximately 300,000 Daltons) in phosphate buffered saline. The bone component is added to achieve a bone concentration of 30%(w/w). The solution is well mixed and allowed to stand for 2–3 hours at room temperature. This provides a malleable putty with excellent formability properties.

Example VII

A malleable putty of Dextran 40 PM 20% with 100–800 micron demineralized cortical allograft bone powder having a residual calcium weight of 3 to 8% @ 33% total weight percentage of the composition.

The example was formulated with 0.502 grams of freeze dried demineralized cortical allograft bone of particle size of 100–800 microns mixed into 1.006 grams of a 20% solution of Dextran 40 PM (mol.wt. approximately 40,000 Daltons) in phosphate buffered saline. The bone component is added to achieve a bone concentration of 33%(w/w). The solution is well mixed and allowed to stand for 2–3 hours at room temperature. This provides a malleable putty with excellent formability properties.

Example VIII

A malleable putty of Dextran 40 PM 20% with 100–800 micron demineralized cortical allograft bone powder having a residual calcium weight of 3 to 8% @ 50% total weight percentage of the composition.

The example was formulated with 1.37 grams of freeze dried demineralized cortical allograft bone of particle size of 100–800 microns mixed into 1.36 grams of a 20% solution of Dextran 40 PM (mol. wt. Approximately 40,000 Daltons) in phosphate buffered saline. The bone component is added to achieve a bone concentration of 50%(w/w). The solution is well mixed and allowed to stand for 2–3 hours at room temperature. This provides a malleable putty with poor formability properties.

Example IX

A malleable putty of Hydroxypropylmethylcellulose (HPMC) 6% with 100–800 micron demineralized cortical allograft bone powder having a residual calcium weight of 3 to 8% @ 33% total weight percentage of the composition.

The example was formulated with 1 gram of freeze dried cortical allograft bone of particle size of 100–800 microns mixed into 2.006 grams of a 6% solution of HPMC (mol.wt. approx. 100,000 Daltons) in phosphate buffered saline. The bone component is added to achieve a bone concentration of 33%(w/w). The solution is well mixed and allowed to stand for 2–3 hours at room temperature. This provides a malleable putty with good formability properties.

Example X

A malleable putty of Carboxymethylcellulose (CMC) 6% with 100–800 micron cortical demineralized allograft bone powder having a residual calcium weight of 3 to 8% @ 33% total weight percentage of the composition.

The example was formulated with 0.8 gram of freeze dried demineralized cortical allograft bone of particle size of 100–800 microns mixed into 1.6 grams of a 6% solution of CMC (mol. wt. 30,000 Daltons) in phosphate buffered saline. The bone component is added to achieve a bone concentration of 33%(w/w). The solution is well mixed and allowed to stand for 2–3 hours at room temperature. This provides a malleable putty with satisfactory formability properties.

Example XI

A malleable putty of chitosan 3% with 100–800 micron cortical allograft bone powder having a residual calcium weight of 3 to 8% @ 33% total weight percentage of the composition.

The example was formulated with 1 gram of freeze dried cortical allograft bone of particle size of 100–800 microns mixed into 2.002 grams of a 3% solution of chitosan (mol. wt. approx. 300,000 Daltons) in normal saline. The bone component is added to achieve a bone concentration of 33%(w/w). The solution is well mixed and allowed to stand for 2–3 hours at room temperature. This provides a malleable putty with good formability properties.

Example XII

A malleable putty of chitosan 3% with 100–800 micron cortical allograft bone powder having a residual calcium weight of 3 to 8% @ 33% total weight percentage of the composition.

The example was formulated with 1.3 grams of freeze dried demineralized cortical allograft bone of particle size of 100–800 microns mixed into 2.58 grams of a 3% solution of chitosan (mol. wt. approx. 300,000 Daltons) in normal saline. The bone component is added to achieve a bone concentration of 33%(w/w). The solution is well mixed and allowed to stand for 2–3 hours at room temperature. This provides a malleable putty with good formability properties.

Example XIII

A malleable putty of chitosan 3% with 100–800 micron demineralized cortical allograft bone powder having a residual calcium weight of 3 to 8% @ 50% total weight percentage of the composition.

The example was formulated with 1 gram of freeze dried demineralized cortical allograft bone of particle size of 100–800 microns mixed into 1.02 grams of a 3% solution of chitosan (mol.wt. approx. 300,000 Daltons) in normal saline. The bone component is added to achieve a bone concentration of 50%(w/w). The solution is well mixed and allowed to stand for 2–3 hours at room temperature. This provides a malleable putty with poor formability properties.

Example XIV

A flowable paste of 100–800 micron particle size demineralized cortical allograft bone powder having a residual calcium weight of 3 to 8% in a 3% solution of sodium alginate at a 26% bone total weight percentage of the composition.

The example was formulated with 0.5 grams of allograft freeze dried demineralized cortical bone mixed into 1.42 grams of a 3% solution of sodium alginate (mol.wt. approx. 300,000 Daltons) in phosphate buffered saline. The bone component is added to achieve a bone concentration of 26% (w/w). The solution is well mixed and allowed to stand for 2–3 hours at room temperature. This provides a viscous, non-flowable paste.

Example XV

A flowable paste of 100–800 micron particle size demineralized cortical allogratt bone powder having a residual calcium weight of 3 to 8% in a 3% solution of sodium alginate at a 25% (w/w) bone total weight percentage of the composition.

The example was formulated with 0.5 grams of allograft freeze dried demineralized cortical bone mixed into 1.5 grams of a 3% solution of sodium alginate (mol.wt. approx. 300,000 Daltons) in phosphate buffered saline. The bone component is added to achieve a bone concentration of 25% (w/w). The solution is well mixed and allowed to stand for 2–3 hours at room temperature. This provides a viscous, non-flowable paste.

Example XVI

A flowable paste of HPMC 3% with 100–800 micron demineralized cortical allograft bone powder having a residual calcium weight of 3 to 8% @ 25% bone total weight percentage of the composition.

The example was formulated with 1 gram of freeze dried cortical allograft bone of particle size of 100–300 microns mixed into 3 grams of a 3% solution of HPMC (mol.wt. approx. 100,000 Daltons) in phosphate buffered saline. The bone component is added to achieve a bone concentration of 25%(w/w). The solution is well mixed and allowed to stand for 2–3 hours at room temperature. This provides a slightly viscous, flowable paste.

Example XVII

A flowable paste of 100–800 micron particle size demineralized cortical allograft bone powder having a residual calcium weight of 3 to 8% in a 2% solution of chitosan at a 27% (w/w)bone total weight percentage of the composition.

The example was formulated with 0.5 grams of allograft freeze-dried cortical bone mixed into 1.352 grams of a 2% solution of chitosan (mol.wt. approx. 300,000 Daltons) in normal saline. The bone component is added to achieve a bone concentration of 27% (w/w). The solution is well mixed and allowed to stand for 2–3 hours at room temperature. This provides a dry, non-flowable paste.

Example XVIII

A flowable paste of 100–800 micron particle size demineralized cortical allograft bone powder having a residual calcium weight of 3 to 8% in a 3% solution of CMC at a 25% (w/w) bone total weight percentage of the composition.

The example was formulated with 1 gram of allograft freeze dried demineralized cortical bone mixed to 3 grams of a 3% solution of CMC (mol. Wt. approx. 300,000 Daltons) in phosphate buffered saline. The bone component is added to achieve a bone concentration of 25%(w/w). The solution is well mixed and allowed to stand for 2–3 hours at room temperature. This provides a flowable paste.

Example XIX

A flowable paste of 100–800 micron particle size demineralized cortical allograft bone powder having a residual calcium weight of 3 to 8% in a 10% solution of Dextran 40 PM at a 25% (w/w)bone total weight percentage of the composition.

The example was formulated with 0.75 grams of allograft freeze dried demineralized cortical bone mixed with 2.25 grams of a 10% solution of Dextran 40 PM in phosphate buffered saline. The bone component is added to achieve a bone concentration of 25% (w/w). The solution is well mixed and allowed to stand for 2–3 hours at room temperature. This provides a slightly runny, flowable paste.

Example XX

A flowable paste of 100–800 micron particle size demineralized cortical allograft bone powder having a residual calcium weight of 3 to 8% in a 10% solution of Dextran 40 PM at a 27% (w/w) bone total weight percentage of the composition.

The example was formulated with 0.81 grams of allograft freeze dried demineralized cortical bone mixed with 2.19 grams of a 10% solution of Dextran 40 PM in phosphate buffered saline. The bone component is added to achieve a bone concentration of 27% (w/w). The solution is well mixed and allowed to stand for 2–3 hours at room temperature. This provides a slightly runny, flowable paste.

Example XXI

A flowable paste of 100–800 micron particle size demineralized cortical allograft bone powder having a residual calcium weight of 3 to 8% in a 15% solution of Dextran 40 PM at a 25% (w/w) bone total weight percentage of the composition.

The example was formulated with 0.75 grams of allograft freeze dried demineralized cortical bone mixed with 2.25 grams of a 15% solution of Dextran 40 PM in phosphate buffered saline. The bone component is added to achieve a bone concentration of 25% (w/w). The solution is well mixed and allowed to stand for 2–3 hours at room temperature. This provides a flowable paste.

Example XXII

A flowable pastel of 100–800 micron particle size demineralized cortical allograft bone powder having a residual calcium weight of 3 to 8%. in a 15% solution of Dextran 40 PM at a 27% (w/w) bone total weight percentage of the composition.

The example was formulated with 0.81 grams of allograft freeze dried demineralized cortical bone mixed with 2.19 grams of a 15% solution of Dextran 40 PM in phosphate buffered saline. The bone component is added to achieve a bone concentration of 27% (w/w). The solution is well mixed and allowed to stand for 2–3 hours at room temperature. This provides a flowable paste.

Example XXIII

A flowable paste of 100–800 micron particle size demineralized cortical allograft bone powder having a residual calcium weight of 3 to 8% in a 1% solution of sodium alginate at a 25% (w/w) bone total weight percentage of the composition.

The example was formulated with 0.75 grams of allograft freeze dried demineralized cortical bone mixed with 2.25 grams of a 1% solution of sodium alginate in phosphate buffered saline. The bone component is added to achieve a bone concentration of 25% (w/w). The solution is well mixed and allowed to stand for 2–3 hours at room temperature. This provides a flowable paste.

Example XXIV

A flowable paste of 100–800 micron particle size demineralized cortical allograft bone powder having a residual calcium weight of 3 to 8% in a 1% solution of sodium alginate at a 27% (w/w) bone total weight percentage of the composition.

The example was formulated with 0.81 grams of allograft freeze dried demineralized cortical bone mixed with 2.19 grams of a 1% solution of sodium alginate in phosphate buffered saline. The bone component is added to achieve a bone concentration of 27% (w/w). The solution is well mixed and allowed to stand for 2–3 hours at room temperature. This provides a flowable paste.

Example XXV

A flowable paste of 100–800 micron particle size demineralized cortical allograft bone powder having a residual calcium weight of 3 to 8% in a 2% solution of sodium alginate at a 25% (w/w) bone total weight percentage of the composition.

The example was formulated with 0.75 grams of allograft freeze dried demineralized cortical bone mixed with 2.25 grams of a 2% solution of sodium alginate in phosphate buffered saline. The bone component is added to achieve a bone concentration of 25% (w/w). The solution is well mixed and allowed to stand for 2–3 hours at room temperature. This provides a flowable paste.

Example XXVI

A flowable paste of 100–800 micron particle size demineralized cortical allograft bone powder having a residual calcium weight of 3 to 8% in a 2% solution of sodium alginate at a 27% (w/w) bone total weight percentage of the composition.

The example was formulated with 0.81 grams of allograft freeze dried demineralized cortical bone mixed with 2.19 grams of a 2% solution of sodium alginate in phosphate buffered saline. The bone component is added to achieve a bone concentration of 27% (w/w). The solution is well mixed and allowed to stand for 2–3 hours at room temperature. This provides a slightly viscous, flowable paste.

B. Mailable Putty of Partially Demineralized Cortical and/or Cortical/Cancellous Allograft Bone

Example XXVII

A DBX mix of sodium hyaluronate 4% with coarsely milled demineralized cortical/cancellous allograft bone having a residual calcium weight of 3 to 8% @ 33% total weight percentage of the composition.

The coarsely milled cortical/cancerous demineralized chips are in the form of irregularly shaped polyhedra with edge dimensions up to about 5 mm. 2.2 gram of demineralized cortical cancerous allograft granules and 1.1 grams of demineralized cortical powder were mixed into 6.7 grams of 4% sodium hyaluronate (4% mol. Wt. approx. 700,000 Daltons) in phosphate buffered saline, and mixed well until it appears uniform and no dry bone is present. The bone components are added to achieve a bone concentration of 33%(w/w). The mixture is allowed to stand for 2–3 hours at room temperature to achieve a well-equilibrated mixture. This provides a malleable putty with excellent formability properties and gave a texture of smooth putty with bone chips, and is an excellent bone void filler.

Example XXVIII

A DBX mix of sodium hyaluronate 4% with coarsely milled demineralized cortical/cancellous allograft bone having a residual calcium weight of 3 to 8%@ 30% total weight percentage of the composition.

The coarsely milled cortical/cancerous demineralized chips are in the form of irregularly shaped polyhedra with edge dimensions up to about 5 mm. 3.0 grams of demineralized coarsely milled cortical cancellous allograft and 7.0 grams of 4% sodium hyaluronate (4% mol. Wt. approx. 700,000 Daltons) in phosphate buffered saline, and mixed well until it appears uniform and no dry bone is present The bone components are added to achieve a bone concentration of 30%(w/w). The mixture is allowed to stand for 2–3 hours at room temperature to achieve an well-equilibrated mixture. This provides a malleable paste with good formability properties and gave a texture of smooth putty with bone chips and is a good bone void filler.

Example XXIX

A DBX mix of sodium hyaluronate 4% with coarsely milled demineralized cortical/cancellous allograft bone having a residual calcium weight of 3 to 8% @ 35% total weight percentage of the composition.

The coarsely milled cortical/cancellous demineralized chips are in the form of irregularly shaped polyhedra with edge dimensions up to about 5 mm. 7.0 grams of demineralized coarsely milled cortical cancellous allograft and 13.0 grams of 4% sodium hyaluronate (4% mol. Wt. approx. 700,000 Daltons) in phosphate buffered saline, and mixed well until it appears uniform and no dry bone is present. The bone components are added to achieve a bone concentration of 35%(w/w). The mixture is allowed to stand for 2–3 hours at room temperature to achieve a well-equilibrated mixture. This provides a malleable putty with excellent formability properties and gave an excellent texture of smooth putty with bone chips and is a good bone void filler for large defects.

Example XXX

A DBX mix of sodium hyaluronate 4% with coarsely milled demineralized cortical/cancellous allograft bone having a residual calcium weight of 3 to 8% @ 37.5% total weight percentage of the composition.

The coarsely milled cortical/cancellous demineralized chips are in the form of irregularly shaped polyhedra with edge dimensions up to about 5 mm. 1.88 grams of demineralized coarsely milled cortical cancellous allograft and 3.13 grams of 4% sodium hyaluronate (4% mol. Wt. approx. 700,000 Daltons) in phosphate buffered saline, and mixed well until it appears uniform and no dry bone is present. The bone components are added to achieve a bone concentration of 37.5%(w/w). The mixture is allowed to stand for 2–3 hours at room temperature to achieve a well-equilibrated mixture. This provides a putty with good formability properties and gave a good texture of smooth putty with bone chips and is an excellent void filler.

Example XXXI

A DBX mix of sodium hyaluronate 4% with coarsely milled demineralized cortical cancellous allograft bone having a residual calcium weight of 3 to 8%@ 50% total weight percentage of the composition.

The coarsely milled cortical/cancerous demineralized chips are in the form of irregularly shaped polyhedra with edge dimensions up to about 5 mm. 0.932 g of demineralized coarsely milled cortical/cancellous allograft and 0.932 g of 4% sodium hyaluronate (4% mol. Wt. approx. 700,000 Daltons) in phosphate buffered saline, and mixed well until it appears uniform and no dry bone is present. The bone components are added to achieve a bone concentration of 50% (w/w). The mixture is allowed to stand for 2–3 hours at room temperature to achieve a well-equilibrated mixture. This provides a malleable putty with poor formability properties. The sample was too dry and did not stick together.

The coarsely milled cortical/cancellous demineralized chips noted in Examples 27 through 31 listed above can be substituted in part or totally for the gram weight of the freeze dried cortical allograft bone listed in Examples 6 through 13 and achieve the same formability properties noted therein.

Example XXXII

A malleable putty of gelatin 6% with 100–800 micron sized demineralized cortical allograft bone powder having a residual calcium weight of 3 to 8% constituting @ 33% total weight percentage of the composition.

The example was formulated with 1 gram of freeze dried demineralized cortical allograft bone of particle size of 100–800 microns mixed into 2.002 grams of a 6% solution of gelatin in phosphate buffered saline. The bone component is added to achieve a bone concentration of 33%(w/w). The solution is well mixed and allowed to stand for 2–3 hours at room temperature. This provides a malleable putty with good formability properties.

Example XXXIII

A malleable putty of gelatin 4% with 100–800 micron sized demineralized cortical allograft bone powder having a residual calcium weight of 3 to 8% constituting @ 33% total weight percentage of the composition.

The example was formulated with 1 gram of freeze dried demineralized cortical allograft bone of particle size of 100–800 microns mixed into 2.002 grams of a 4% solution of gelatin in phosphate buffered saline. The bone component is added to achieve a bone concentration of 33%(w/w). The solution is well mixed and allowed to stand for 2–3 hours at room temperature. This provides a malleable putty with acceptable formability properties.

Example XXXIV

A malleable putty of gelatin 6% with 100–800 micron sized demineralized cortical allograft bone powder having a residual calcium weight of 3 to 8% constituting @ 50% total weight percentage of the composition.

The example was formulated with 1 gram of freeze dried demineralized cortical allograft bone of particle size of 100–800 microns mixed into 1.00 gram of a 6% solution of gelatin in phosphate buffered saline. The bone component is added to achieve a bone concentration of 50%(w/w). The solution is well mixed and allowed to stand for 2–3 hours at room temperature. This provides a malleable putty with poor formability properties, but acceptable for a bone filler.

Example XXXV

A malleable putty of collagen 4% with 100–800 micron sized demineralized cortical allograft bone powder having a residual calcium weight of 3 to 8% constituting @ 33% total weight percentage of the composition.

The example was formulated with 1 gram of freeze dried demineralized cortical allograft bone of particle size of 100–800 microns mixed into 2.0 grams of a 4% solution of collagen in phosphate buffered saline at pH 3.3. The bone component is added to achieve a bone concentration of 33%(w/w). The solution is well mixed and allowed to stand for 2–3 hours at room temperature. This provides a malleable putty with satisfactory formability properties, and is acceptable for a bone filler.

Example XXXVI

A malleable putty of gelatin 6% and 4% collagen with 100–800 micron sized demineralized cortical allograft bone powder having a residual calcium weight of 3 to 8% constituting @ 33% total weight percentage of the composition.

The example was formulated with 1.003 grams of freeze dried demineralized cortical allograft bone of particle size of 100–800 microns mixed into 1.004 grams of a 6% solution of gelatin and 1.003 grams of 4% collagen in phosphate buffered saline at pH 3.3. The bone component is added to achieve a bone concentration of 33%(w/w). The solution is well mixed and allowed to stand for 2–3 hours at room temperature. This provides a malleable putty with excellent formability properties.

C. Flowable Bone Paste of Partially Demineralized Cortical Allograft Bone

Example XXXVII

A flowable paste of gelatin 4% with 100–800 micron sized demineralized cortical allograft bone powder having a residual calcium weight of 3 to 8% constituting @ 25% total weight percentage of the composition.

The example was formulated with 0.5 gram of freeze dried demineralized cortical allograft bone of particle size of 100–800 microns mixed into 1.5 grams of a 4% solution of gelatin in phosphate buffered saline. The bone component is added to achieve a bone concentration of 25%(w/w). The solution is well mixed and allowed to stand for 2–3 hours at room temperature. This provides a flowable paste.

Example XXXVIII

A flowable paste of gelatin 6% and 4% collagen with 100–800 micron sized demineralized cortical allograft bone powder having a residual calcium weight of 3 to 8% constituting @ 25% total weight percentage of the composition.

The example was formulated with 0.5 gram of freeze dried demineralized cortical allograft bone of particle size of 100–800 microns mixed into 0.75 gram of a 6% solution of gelatin and 0.75 gram of 4% collagen in phosphate buffered saline at pH 3.3. The bone component is added to achieve a bone concentration of 25%(w/w). The solution is well mixed and allowed to stand for 2–3 hours at room temperature. This provides a flowable paste.

One process commonly used to achieve sterility is sterile filtration of the sodium hyaluronate (HA) followed by aseptic mixing of the bone and HA. Another method is to irradiate the HA material first and then continue with aseptic mixing of the bone. Irradiation sources of either electron beam or gamma (Cobalt 60 isotope) are commercially available.

The use of radiation will reduce the molecular weight of the HA. An HA with much higher molecular weight up to 6,000,000 Daltons would be selected and the irradiation controlled to reduce the molecular weight to a level sufficient to achieve the desired final viscosity. This approach expands the available range of HA molecular weight and concentration useful for the invention.

The mixing of the demineralized bone powder into hydrogel carrier solution is undertaken in a sterile chamber. The mixed malleable bone composition is then placed in a sterile container such as an impervious syringe barrel or vial, sealed and placed in a sterile sealed package.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. A sterile malleable bone composition for application to a bone defect site to promote new bone growth at the site comprising a mixture of partially demineralized osteoinductive and osteoconductive bone material having a calcium content ranging from above 4% to about 8% with a particle size ranging from about 100 to about 800 microns, the bone material ranging from about 25 to about 35% of the weight of the composition, the carrier comprising a hydrogel component in a phosphate buffered aqueous solution, said hydrogel component comprising sodium hyaluronate and its derivatives, and having a high molecular weight ranging from seven hundred thousand to three million Daltons with a stable viscosity from 22° to about 37° C. and ranging from about 0.75% to about 5.0% by weight of the aqueous carrier solution.

2. A malleable bone composition as claimed in claim 1 wherein said mixture includes bone morphogenic protein in excess of the amount naturally occurring in allogeneic bone.

3. A malleable bone composition as claimed in claim 1 wherein said osteoconductive bone material has a calcium content greater than 4%.

4. A malleable bone composition as claimed in claim 1 wherein said phosphate includes two phosphate ions $HPO_4^{-2}$ and $H_2PO_4^{-1}$.

5. A malleable bone composition as claimed in claim 1 wherein said composition has an isotonic state of about 300 mOsmol/Kg.

6. A malleable bone composition as claimed in claim 1 wherein said bone powder contains cortical cancerous bone material.

7. A malleable bone composition as claimed in claim 1 wherein said composition has a pH ranging from about 6.8 to about 7.4.

8. A malleable bone composition as claimed in claim 1 wherein said bone material includes cortical cancellous bone segments coarsely milled into irregular polyhedral shaped chips with edge dimensions up to about 5 mm.

9. A malleable bone composition as claimed in claim 1 wherein said bone powder contains growth factors such as transforming growth factor (TGF-beta), platelet derived growth factor (PDGF), osteopontin, fibroblast growth factor (FGF) and insulin-like growth factor (IGF-1).

10. A malleable bone composition as claimed in claim 1 wherein said bone powder contains living cells such as blood cells, bone marrow cells and mesenchymal stem cells.

11. A sterile malleable bone composition for application to a bone defect site to promote new bone growth at the site which comprises a new bone growth inducing mixture of partially demineralized lyophilized allograft bone powder having a residual calcium content ranging from about 4% to about 8% with a particle size ranging from about 100 to about 800 microns in a sodium hyaluronate with an ionic salt based phosphate buffer carrier causing the composition to have a pH ranging between about 6.8 and about 7.4, the sodium hyaluronate component having a molecular weight of at least seven hundred Daltons and a stable viscosity ranging from 6,000 to about 275,000 cps at 22° to 37° C., the bone content of the carrier ranging in weight from about 20% to less than 50% total weight of the composition.

12. A malleable bone composition as claimed in claim 11 wherein said saline phosphate buffer carrier includes a sodium based phosphate compound.

13. A malleable bone composition as claimed in claim 11 wherein said phosphate includes at least two phosphate ions $HPO_4^{-2}$ and $H_2PO_4^{-1}$.

14. A malleable bone composition as claimed in claim 11 wherein said composition has an isotonic state of about 300 mOsmol/Kg.

15. A malleable bone composition as claimed in claim 1 wherein said bone powder has a residual calcium content above 4%.

16. A malleable bone composition as claimed in claim 11 wherein said sodium hyaluronate has been irradiated.

17. A malleable bone composition as claimed in claim 11 including antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin, gentamycin and vitamins.

18. A malleable bone composition as claimed in claim 11 wherein said composition includes bone morphogenic proteins in excess of the amount naturally occurring in allogeneic bone.

19. A malleable bone composition as claimed in claim 11 wherein said composition has a pH ranging from 6.8 to 7.4.

20. A malleable bone composition as claimed in claim 11 wherein said bone powder contains growth factors such as transforming growth factor (TGF-beta), platelet derived growth factor (PDGF), osteopontin, fibroblast growth factor (FGF) and insulin-like growth factor (IGF-1).

21. A malleable bone composition as claimed in claim 11 wherein said bone powder contains living cells such as blood cells, bone marrow cells and mesenchymal stem cells.

22. A sterile malleable bone putty composition for application to a bone defect site to promote new bone growth at the site comprising a new bone growth inducing partially demineralized lyophilized allograft bone powder with a residual calcium content of about 4% to 5% and a particle size ranging from about 100 to about 800 microns in a high molecular weight sodium hyaluronate and saline phosphate buffer carrier, the bone content of the composition ranging from about 30% to about 35% by weight with the sodium hyaluronate component constituting a percentage of the carrier not in excess of 5% and has a molecular weight greater than 700,000 Daltons.

23. A malleable bone composition as claimed in claim 22 wherein said composition has a pH ranging from about 7.2 to about 7.4.

24. A malleable bone composition as claimed in claim 22 wherein said composition has an isotonic state of about 300 mOsmol/Kg.

25. A malleable bone composition as claimed in claim 22 wherein said bone powder contains growth factors such as transforming growth factor (TGF-beta), platelet derived growth factor (PDGF), osteopontin, fibroblast growth factor (FGF) and insulin-like growth factor (IGF-1).

26. A malleable bone composition as claimed in claim 22 wherein said bone powder contains living cells such as blood cells, bone marrow cells and mesenchymal stem cells.

27. A sterile malleable bone gel composition for application to a bone defect site to promote new bone growth at the site which comprises a new bone growth inducing amount of partially demineralized lyophilized allograft bone material with a residual calcium content of above 4% to about 6% dry weight and a particle size ranging from about 100 to about 800 microns in a high molecular weight sodium hyaluronate having a molecular weight of at least about seven hundred thousand Daltons in saline phosphate buffer carrier with the sodium hyaluronate component comprising about 1.0% to about 4.0% of the carrier and having a viscosity of about 1,800 to 13,000 cps, the bone powder content of the composition ranging from about 25% to about 30% with said composition having an osmolality ranging from about 280 to about 340 mOsmol/Kg.

28. A malleable bone composition as claimed in claim 27 wherein said composition includes bone morphogenic proteins in excess of the amount naturally occurring in allogeneic bone.

29. A malleable bone composition as claimed in claim 27 wherein said phosphate includes two phosphate ions $HPO_4^{-2}$ and $H_2PO_4^{-1}$.

30. A malleable bone composition as claimed in claim 27 wherein said composition has an isotonic state of about 300 mOsmol/Kg.

31. A malleable bone composition as claimed in claim 27 wherein said bone material contains cortical allograft bone powder.

32. A malleable bone composition as claimed in claim 27 wherein said bone material includes cortical cancerous allograft bone powder.

33. A malleable bone composition as claimed in claim 27 wherein said composition has a pH ranging from about 7.2 to about 7.4.

34. A malleable bone composition as claimed in claim 27 wherein said bone material includes cortical cancerous bone segments coarsely milled into irregular polyhedral shaped chips with edge dimensions up to about 5 mm.

35. A malleable bone composition as claimed in claim 27 wherein said bone powder contains growth factors such as transforming growth factor (TGF-beta), platelet derived growth factor (PDGF), osteopontin, fibroblast growth factor (FGF) and insulin-like growth factor (IGF-1).

36. A malleable bone composition as claimed in claim 27 wherein said bone powder contains living cells such as blood cells, bone marrow cells and mesenchymal stem cells.

37. A sterile malleable bone putty composition for application to a bone defect site to promote new bone growth at the site which comprises a new bone growth inducing compound of partially demineralized lyophilized allograft bone material with a calcium content greater than 4% and less than 8% dry weight and a particle size ranging from about 100 to about 800 microns in a hydrogel ionic salt based phosphate buffer carrier, a hydrogel component comprising a glycosaminoglycan ranging from about 2.0% to about 5.0% by weight of the carrier and having a molecular weight of at least 700,000 Daltons.

38. A malleable bone composition as claimed in claim 37 wherein said glycosaminoglycan is sodium hyaluronate and its derivatives.

39. A sterile malleable bone putty composition as claimed in claim 37 wherein said carrier has a viscosity ranging from 120,000 to 275,000 cps at 22° to 37° C.

40. A sterile malleable bone putty composition for application to a bone defect site to promote new bone growth at the site which comprises a new bone growth inducing amount of partially demineralized lyophilized allograft bone powder having a residual calcium content of about 4% dry weight in a high molecular weight hydrogel in saline phosphate buffer solution carrier, said hydrogel comprising a glycosaminoglycan having a molecular weight of at least 700,000 Daltons, the bone amount content of the composition ranging from about 27% to about 33% by weight and the high molecular weight hydrogel ranges from about 2.0% to about 5.0% by weight of the carrier, said composition having an osmolality ranging from 280–340 mOsmol/Kg.

41. A sterile malleable bone putty composition as claimed in claim 40 wherein said carrier has a stable viscosity ranging from 120,000 to 275,000 cps at 22° to 37° C.

42. A sterile malleable bone putty composition as claimed in claim 40 wherein said carrier has a stable viscosity ranging from 6,000 to about 275,000 cps at 22° to 37° C.

43. A sterile malleable bone putty composition for application to a bone defect site to promote new bone growth at the site which comprises a new bone growth inducing mixture of partially demineralized lyophilized allograft bone powder having a residual calcium content ranging from greater than 4% to about 8% with a particle size ranging from about 100 to about 800 microns in a hydrogel with an ionic salt based phosphate buffer carrier causing the composition to have a pH ranging between about 7.2 and about 7.4, said hydrogel comprising a polysaccharide selected from the group consisting of sodium hyaluronate, chitosan, sodium alginate, carboxymethylcellulose and hydroxypropylmethylcellulose, said hydrogel component having a molecular weight of at least twenty thousand Daltons and a stable viscosity ranging from 6,000 to about 275,000 cps at 22° to 37° C., the bone content of the carrier ranging in weight from about 20% to less than 50% total weight of the composition.

44. A sterile malleable bone putty composition as claimed in claim 43 wherein the bone amount content of the composition ranges from about 30% to about 38% by weight and the high molecular weight hydrogel ranges from about 2.0% to about 5.0% by weight of the carrier, said composition having a pH ranging from about 7.2 to about 7.4.

45. A sterile malleable bone composition for application to a bone defect site to promote new bone growth at the site which comprises a new bone growth inducing amount of partially demineralized lyophilized human allograft bone material having a residual calcium content of at least 4% to about 8% in a high molecular weight hydrogel and saline phosphate buffer solution carrier, said hydrogel comprising a sodium hyaluronate or its derivatives having a molecular weight of at least 3,000,000 Daltons, the bone amount content of the composition ranging from about 25% to about 35% by weight and the high molecular weight hydrogel ranging from about 0.25% to about 1.5% by weight of the carrier, said composition having a pH ranging from about 7.2 to about 7.4.

46. A sterile malleable bone putty composition as claimed in claim 45 wherein said bone material includes cortical cancellous bone segments coarsely milled into irregular polyhedral shaped chips with edge dimensions up to about 5 mm.

47. A sterile malleable bone composition for application to a bone defect site to promote new bone growth at the site which comprises a new bone growth inducing amount of partially demineralized lyophilized human allograft bone material having a residual calcium content of at least 4% to about 8% mixed in a hydrogel and saline solution carrier, said hydrogel selected from a group consisting of chitosan and sodium alginate having a molecular weight ranging from 100,000 to about 300,000 Daltons, the bone amount content of the composition ranging from about 25% to about 50% by weight and the hydrogel ranging from about 1.0% to about 5.0% by weight of the carrier, said composition having a pH ranging from about 7.2 to about 7.4.

48. A sterile malleable bone composition as claimed in claim 47 wherein said bone material includes cortical cancellous bone segments coarsely milled into irregular polyhedral shaped chips with edge dimensions up to about 5 mm.

49. A sterile malleable bone composition for application to a bone defect site to promote new bone growth at the site which comprises a new bone growth inducing amount of demineralized lyophilized human allograft bone material having a residual calcium content of about 4% to about 8% in a hydrogel and saline phosphate buffer solution carrier, said hydrogel comprising a Dextran having a molecular weight of at least 40,000 Daltons, the bone amount content of the composition ranging from about 25% to about 50% by weight and the hydrogel ranging from about 10.0% to about 20.0% by weight of the carrier, said composition having a pH ranging from about 7.2 to about 7.4.

50. A sterile malleable bone composition as claimed in claim 49 wherein said bone material includes cortical cancerous bone segments coarsely milled into irregular polyhedral shaped chips with edge dimensions up to about 5 mm.

51. A sterile malleable bone composition as claimed in claim 49 wherein said bone material has a particle size ranging from about 100 to about 800 microns.

52. A sterile malleable bone composition for application to a bone defect site to promote new bone growth at the site which comprises a new bone growth inducing amount of demineralized lyophilized human allograft bone material having a residual calcium content of about 4% to about 8% in a hydrogel and saline phosphate buffer solution carrier, said hydrogel selected from a group consisting of hydroxypropylmethylcellulose and carboxymethylcellulose having a molecular weight ranging from 20,000 to 100,000 Daltons, the bone amount content of the composition ranging from about 25% to about 35% by weight and the hydrogel ranging from about 4.0% to about 6.0% by weight of the carrier, said composition having a pH ranging from about 7.2 to about 7.4.

53. A sterile malleable bone composition as claimed in claim 52 wherein said bone material includes cortical cancerous bone segments coarsely milled into irregular polyhedral shaped chips with edge dimensions up to about 5 mm.

54. A sterile malleable bone composition as claimed in claim 52 wherein said bone material has a particle size ranging from about 100 to about 800 microns.

55. A sterile malleable bone putty composition for application to a bone defect site to promote new bone growth at the site which comprises a new bone growth inducing compound of partially demineralized lyophilized allograft bone material with a calcium content greater than 4% and less than 8% dry weight and a particle size ranging from about 100 to about 800 microns in a gelatin ionic salt based phosphate buffer carrier, the gelatin ranging from about 4.0% to about 6.0% by weight of the carrier.

56. A malleable bone composition as claimed in claim 55 wherein said composition has a pH ranging from about 7.2 to about 7.4.

57. A malleable bone composition as claimed in claim 55 wherein said bone material includes cortical cancerous bone segments coarsely milled into irregular polyhedral shaped chips with edge dimensions up to about 5 mm.

58. A malleable bone composition as claimed in claim 55 wherein said bone powder contains growth factors such as transforming growth factor (TGF-beta), platelet derived growth factor (PDGF), osteopontin, fibroblast growth factor (FGF) and insulin-like growth factor (IGF-1).

59. A malleable bone composition as claimed in claim 55 wherein said bone powder contains living cells such as blood cells, bone marrow cells and mesenchymal stem cells.

60. A sterile malleable bone putty composition for application to a bone defect site to promote new bone growth at the site which comprises a new bone growth inducing compound of partially demineralized lyophilized allograft bone material with a calcium content greater than 4% and less than 8% dry weight and a particle size ranging from about 100 to about 800 microns in a collagen ionic salt based phosphate buffer carrier, the collagen being about 4.0% by weight of the carrier.

61. A malleable bone composition as claimed in claim 60 wherein said composition has a pH ranging from about 7.2 to about 7.4.

62. A malleable bone composition as claimed in claim 60 wherein said bone material includes cortical cancerous bone segments coarsely milled into irregular polyhedral shaped chips with edge dimensions up to about 5 mm.

63. A malleable bone composition as claimed in claim 60 wherein said bone powder contains growth factors such as transforming growth factor (TGF-beta), platelet derived growth factor (PDGF), osteopontin, fibroblast growth factor (FGF) and insulin-like growth factor (IGF-1).

64. A malleable bone composition as claimed in claim 60 wherein said bone powder contains living cells such as blood cells, bone marrow cells and mesenchymal stem cells.

65. A sterile malleable bone putty composition for application to a bone defect site to promote new bone growth at the site which comprises a new bone growth inducing compound of partially demineralized lyophilized allograft bone material with a calcium content greater than 4% and less than 8% dry weight and a particle size ranging from about 100 to about 800 microns in a gelatin and collagen ionic salt based phosphate buffer carrier, the gelatin being about 6.0% by weight of the carrier and the collagen being about 4.0% by weight of the carrier.

66. A malleable bone composition as claimed in claim 65 wherein said composition has a pH ranging from about 7.2 to about 7.4.

67. A malleable bone composition as claimed in claim 65 wherein said bone material includes cortical cancerous bone segments coarsely milled into irregular polyhedral shaped chips with edge dimensions up to about 5 mm.

68. A malleable bone composition as claimed in claim 65 wherein said bone powder contains growth factors such as transforming growth factor (TGF-beta), platelet derived growth factor (PDGF), osteopontin, fibroblast growth factor (FGF) and insulin-like growth factor (IGF-1).

69. A malleable bone composition as claimed in claim 65 wherein said bone powder contains living cells such as blood cells, bone marrow cells and mesenchymal stem cells.

70. A sterile malleable bone putty composition for application to a bone defect site to promote new bone growth at the site which comprises a new bone growth inducing compound of partially demineralized lyophilized allograft bone material with a calcium content greater than 4% and less than 8% dry weight and a bone component particle size ranging from about 100 to about 800 microns to achieve a bone concentration ranging from about 25% to about 33% (w/w) in a gelatin and collagen ionic salt based phosphate buffer carrier, the combined weight of the gelatin and the collagen being about 10.0% by weight of the carrier.

* * * * *

UNITED STATES PATENT AND TRADEMARK OFFICE
CERTIFICATE OF CORRECTION

PATENT NO. : 6,911,212 B2
DATED : June 28, 2005
INVENTOR(S) : Gertzman and Sunwoo It is certified that error appears in the above-identified patent and that said Letters Patent is hereby corrected as shown below:

<u>Title page,</u>
Item [57], ABSTRACT,
Line 2, the word "pastel" should read -- paste --.
Line 11, the figure "50%" should read -- 5.0% --.

<u>Column 6,</u>
Line 42, the word "relatoin" should read -- relation --.

<u>Column 14,</u>
Line 22, the word and figure "of3" should read -- of 3 --.

<u>Column 17,</u>
Line 50, the word "mailable" should read -- malleable --.

<u>Column 21,</u>
Line 42, the word "cancerous" should read -- cancellous --.

Signed and Sealed this

Twenty-fifth Day of October, 2005

JON W. DUDAS
*Director of the United States Patent and Trademark Office*